(12) United States Patent
Miyai

(10) Patent No.: US 10,827,906 B2
(45) Date of Patent: Nov. 10, 2020

(54) ENDOSCOPIC SURGERY IMAGE PROCESSING APPARATUS, IMAGE PROCESSING METHOD, AND PROGRAM

(71) Applicant: SONY CORPORATION, Tokyo (JP)

(72) Inventor: Takeshi Miyai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 616 days.

(21) Appl. No.: 15/306,775

(22) PCT Filed: Jun. 1, 2015

(86) PCT No.: PCT/JP2015/002748
§ 371 (c)(1),
(2) Date: Oct. 26, 2016

(87) PCT Pub. No.: WO2015/186335
PCT Pub. Date: Dec. 10, 2015

(65) Prior Publication Data
US 2017/0042407 A1   Feb. 16, 2017

(30) Foreign Application Priority Data

Jun. 4, 2014 (JP) .................. 2014-115769

(51) Int. Cl.
*A61B 1/04* (2006.01)
*H04N 5/225* (2006.01)
(Continued)

(52) U.S. Cl.
CPC ...... *A61B 1/00009* (2013.01); *A61B 1/00045* (2013.01); *A61B 1/00193* (2013.01);
(Continued)

(58) Field of Classification Search
CPC ............ A61B 1/00009; A61B 1/00193; A61B 2576/00; A61B 2090/367;
(Continued)

(56) References Cited

U.S. PATENT DOCUMENTS 5,459,517 A * 10/1995 Kunitake ............... H04N 5/144
348/700
5,649,021 A * 7/1997 Matey ...................... G06K 9/46
348/65

(Continued)

FOREIGN PATENT DOCUMENTS

JP 7-154687 6/1995
JP 11-309 1/1999
(Continued)

OTHER PUBLICATIONS

International Search Report dated Nov. 12, 2015 in corresponding PCT/JP2015/002748.
(Continued)

*Primary Examiner* — John P Leubecker
(74) *Attorney, Agent, or Firm* — Xsensus LLP

(57) ABSTRACT

A medical image processing apparatus including a controller including circuitry configured to determine a position of a distal end of an important object within a medical image, estimate a region of interest within the medical image adjacent to a region including the important object based on the position of the distal end of the important object, and control display of the region of interest.

15 Claims, 13 Drawing Sheets

(51) Int. Cl.
- *A61B 1/00* (2006.01)
- *H04N 5/232* (2006.01)
- *H04N 13/239* (2018.01)
- *G02B 23/24* (2006.01)
- *G05B 19/402* (2006.01)
- *G06F 19/00* (2018.01)
- *H04N 13/00* (2018.01)

(52) U.S. Cl.
CPC ............ *A61B 1/04* (2013.01); *G02B 23/2415* (2013.01); *G02B 23/2484* (2013.01); *G05B 19/402* (2013.01); *G06F 19/321* (2013.01); *H04N 5/2256* (2013.01); *H04N 5/23212* (2013.01); *H04N 13/239* (2018.05); *G05B 2219/45123* (2013.01); *H04N 2005/2255* (2013.01); *H04N 2013/0081* (2013.01)

(58) Field of Classification Search
CPC .... H04N 2005/2255; H04N 2013/0081; G06T 2207/10068
See application file for complete search history.

(56) References Cited

U.S. PATENT DOCUMENTS

| | | | | |
|---|---|---|---|---|
| 5,820,545 | A * | 10/1998 | Arbter | A61B 1/00147 600/117 |
| 2007/0232863 | A1* | 10/2007 | Miyake | A61B 1/00045 600/204 |
| 2008/0004603 | A1 | 1/2008 | Larkin et al. | |
| 2008/0108873 | A1* | 5/2008 | Gattani | A61B 1/045 600/168 |
| 2008/0266396 | A1* | 10/2008 | Stein | G06K 9/00805 348/148 |
| 2009/0167866 | A1* | 7/2009 | Lee | G06K 9/3233 348/159 |
| 2011/0245660 | A1* | 10/2011 | Miyamoto | A61B 6/032 600/424 |
| 2012/0243733 | A1* | 9/2012 | Sawai | G06T 7/215 382/103 |
| 2013/0018255 | A1* | 1/2013 | Kitamura | A61B 1/00009 600/424 |
| 2013/0023730 | A1* | 1/2013 | Kitamura | A61B 1/00009 600/104 |
| 2013/0104066 | A1 | 4/2013 | Soederstroem | |
| 2013/0259315 | A1* | 10/2013 | Angot | H04N 13/261 382/106 |
| 2014/0005475 | A1* | 1/2014 | Song | A61B 1/3132 600/109 |
| 2014/0031659 | A1* | 1/2014 | Zhao | A61B 5/743 600/371 |
| 2014/0046131 | A1* | 2/2014 | Morita | A61B 1/00179 600/109 |
| 2014/0194896 | A1* | 7/2014 | Frimer | A61B 1/00149 606/130 |
| 2014/0221746 | A1* | 8/2014 | Katayama | A61B 1/00193 600/111 |
| 2015/0077529 | A1 | 3/2015 | Hatta et al. | |
| 2015/0080652 | A1* | 3/2015 | Staples, II | G06F 19/321 600/109 |
| 2015/0215614 | A1* | 7/2015 | Witt | H04N 5/44504 348/45 |
| 2015/0235373 | A1* | 8/2015 | Kato | A61B 1/00009 348/51 |
| 2015/0371376 | A1* | 12/2015 | Adachi | H04N 5/23219 348/140 |
| 2016/0038004 | A1* | 2/2016 | Tanaka | A61B 1/00009 600/371 |
| 2016/0203602 | A1* | 7/2016 | Hayashi | A61B 1/00009 382/128 |
| 2017/0027650 | A1* | 2/2017 | Merck | A61B 1/0005 |
| 2017/0150904 | A1* | 6/2017 | Park | A61B 1/00009 |
| 2017/0180704 | A1* | 6/2017 | Panescu | A61B 90/37 |
| 2017/0181798 | A1* | 6/2017 | Panescu | A61B 34/32 |
| 2017/0265725 | A1* | 9/2017 | Ichikawa | G02B 7/34 |
| 2017/0265726 | A1* | 9/2017 | Mikami | A61B 1/045 |

FOREIGN PATENT DOCUMENTS

| | | |
|---|---|---|
| JP | 2006-215015 | 8/2006 |
| JP | 2009-172050 | 8/2009 |
| JP | 2009-542362 | 12/2009 |
| JP | 2012-75507 | 4/2012 |
| JP | 2012-75508 | 4/2012 |
| JP | 2013-258627 A | 12/2013 |

OTHER PUBLICATIONS

Office Action dated Nov. 30, 2017 in Japanese Patent Application No. 2014-115769.

* cited by examiner

FIG. 4
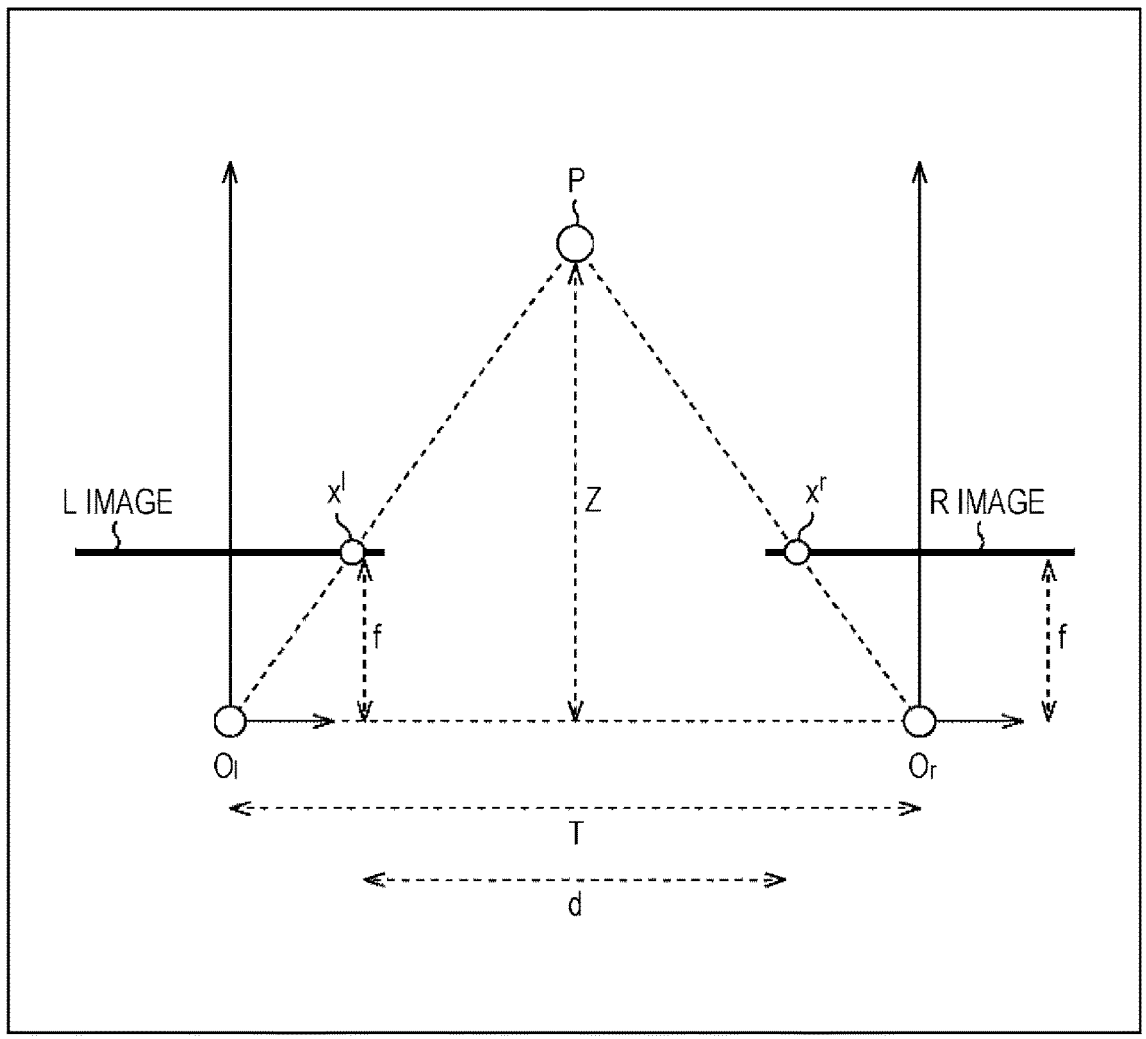
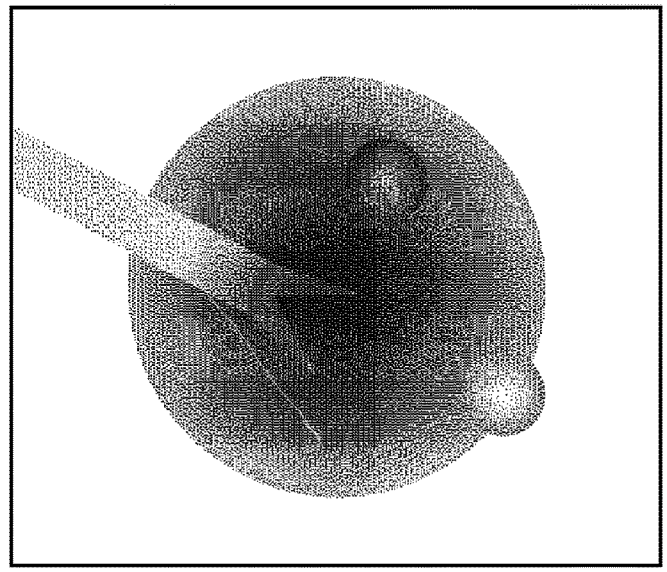
FIG. 5A

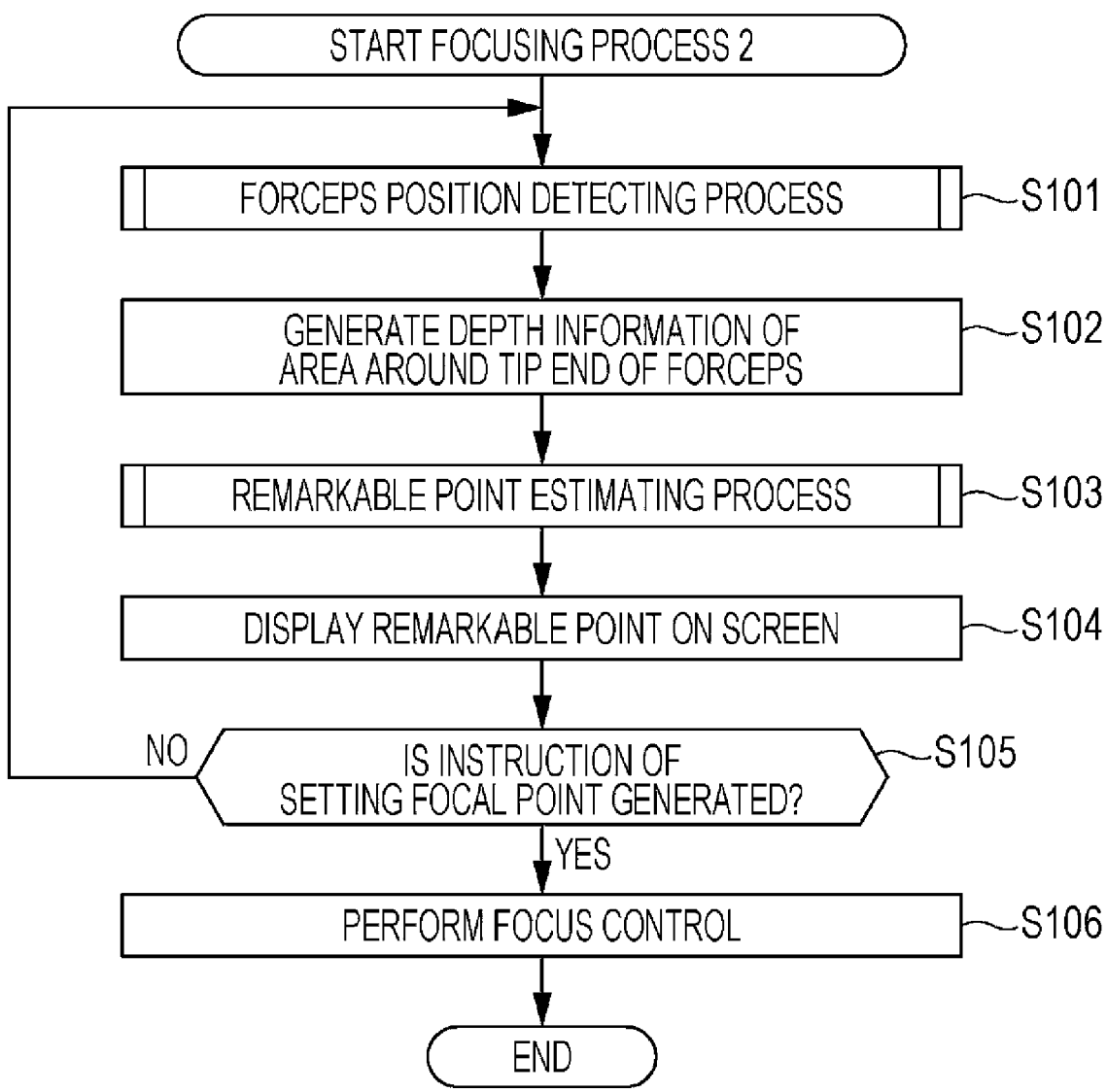

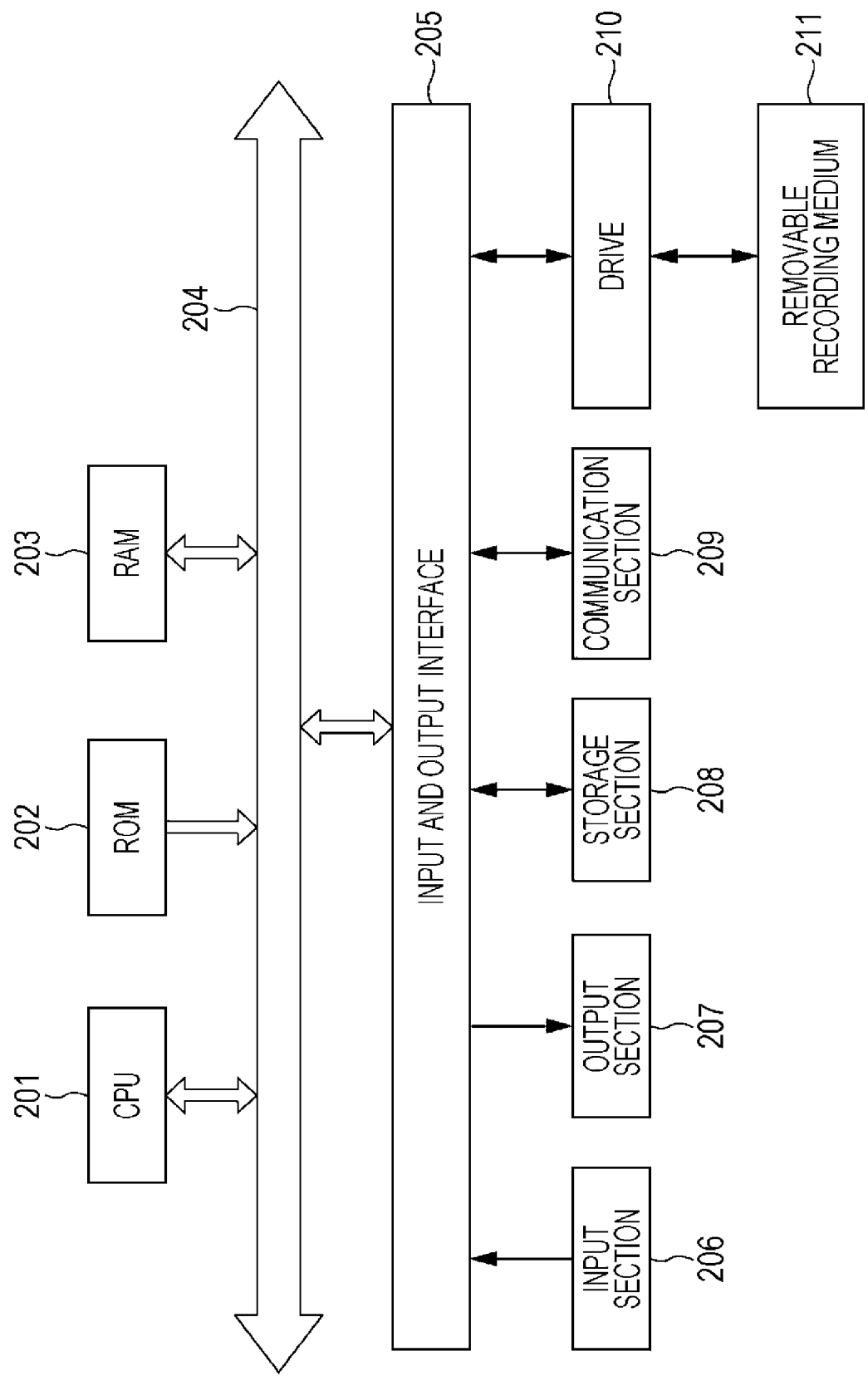

ENDOSCOPIC SURGERY IMAGE PROCESSING APPARATUS, IMAGE PROCESSING METHOD, AND PROGRAM

TECHNICAL FIELD

The present technology relates to an image processing apparatus, an image processing method, and a program, particularly, to an image processing apparatus, an image processing method, and a program allowed to display a surgery region desired by a practitioner without an effort of the practitioner.

CROSS REFERENCE TO RELATED APPLICATIONS

This application claims the benefit of Japanese Priority Patent Application JP 2014-115769 filed Jun. 4, 2014, the entire contents of which are incorporated herein by reference.

BACKGROUND ART

An endoscopic surgery has been used in which an endoscope is inserted into a body, a region (surgery region) being a surgical target in the body is captured as an observed portion to display the captured region on a screen by using the endoscope, and treatment is performed on the surgery region while viewing the screen. In the endoscopic surgery, desired signal processing is performed on an image signal of the observed portion which has an optical image and is obtained in the endoscope by applying illumination light to the observed portion from a light source device and an image of the observed portion having an optical image is displayed on a screen.

In such an endoscopic surgery, it is necessary that a range or a position of an observed portion to be displayed on the screen is appropriately adjusted depending on circumstances in order for a practitioner performing surgery to ensure an optimal view field (surgical field) for a surgery region.

However, typically, the practitioner holds a surgical instrument for performing surgery with both hands. Accordingly, it is difficult for the practitioner to operate a work of such the screen adjustment rapidly for himself. The practitioner operating an adjustment mechanism and the like for himself for screen adjustment is not preferable in view of ensuring a degree of cleanness of a surgery region, medical equipment, an operating room, and the like.

Thus, in general, an instruction of the practitioner is given to an assistant called a scopist or the like and the assistant operates the adjustment mechanism in accordance with the instruction from the practitioner to perform such the screen adjustment.

However, in the method in which the assistant intervenes, the instruction of the practitioner may be transferred inaccurately and thus rapid screen adjustment desired by the practitioner may be difficult.

As a method of adjusting a screen without an assistant intervening, for example, PTL 1 discloses that focus control is performed on an area in which brightness or contrast does not change for a predetermined period.

CITATION LIST

Patent Literature

PTL 1: Japanese Unexamined Patent Application Publication No. 2011-139760

SUMMARY OF INVENTION

Technical Problem

However, according to PTL 1, an area at which brightness or contrast does not change for a predetermined period may or may not be an area which a practitioner wishes to match with a focus and thus an incorrect focus may be obtained.

The present technology is for performing estimation of region of interest desired by a practitioner without an effort of the practitioner in view of such circumstances.

Solution to Problem

According to an embodiment of the present disclosure, there is provided a medical image processing apparatus including a controller including circuitry configured to determine a position of a distal end of an important object within a medical image, estimate a region of interest within the medical image adjacent to a region including the important object based on the position of the distal end of the important object, and control display of the region of interest.

According to another embodiment of the present disclosure, there is provided a method for processing a medical image by a medical image processing apparatus including a controller including circuitry. The method includes the steps of determining, using the circuitry, a position of a distal end of an important object within the medical image, estimating, using the circuitry, a region of interest within the medical image adjacent to a region including the important object based on the position of the distal end of the important object, and controlling, using the circuitry, display of the region of interest.

According to another embodiment of the present disclosure, there is provided a medical image processing system including a medical imaging device that obtains a medical image, a display device having a display area, and a controller including circuitry configured to determine a position of a distal end of an important object within the medical image obtained by the medical imaging device, estimate a region of interest within the medical image adjacent to a region including the important object based on the position of the distal end of the important object, and control display of the region of interest in the display area of the display device.

According to another embodiment of the present disclosure, there is provided a medical image processing apparatus including a controller including circuitry configured to determine a position of an important area within a medical image, estimate a region of interest within the medical image adjacent to a region including the important area based on the position of the important area, and control display of the region of interest.

Advantageous Effects of Invention

According to the embodiments of the present technology, it is possible to perform estimation of region of interest desired by the practitioner.

The effect described herein is not necessarily limited thereto and may include any effect described in the present technology.

BRIEF DESCRIPTION OF DRAWINGS

FIG. 4 is a diagram illustrating the calculation method of the depth position.

FIG. 5A is a diagram illustrating detection of a position of forceps.

FIG. 11 is a flowchart illustrating focus control.

FIG. 12 is a block diagram illustrating a configuration example of an embodiment of a computer according to the present technology.

DESCRIPTION OF EMBODIMENTS

Hereinafter, a configuration (below referred to as an embodiment) for implementing the present technology will be described. The description will be made in the following order.

1. Configuration Example of Endoscope System
2. Flow of Focusing Process
3. The Other Flow of Focusing Process
4. Regarding Recording Medium <Configuration Example of Endoscope System>

Figure 1:
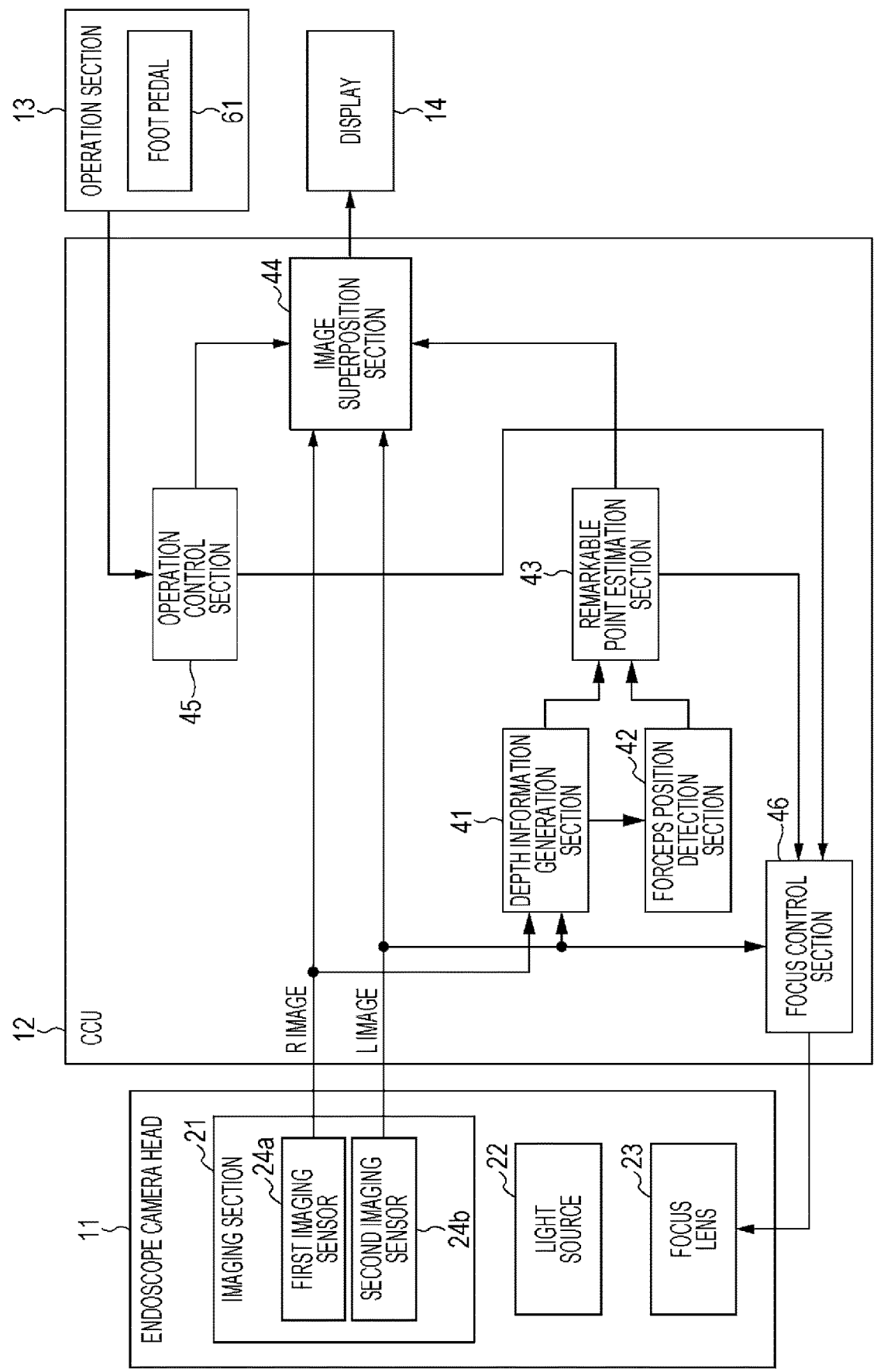
FIG. 1 is a block diagram illustrating a configuration example of an embodiment of an endoscope system according to the present technology.

FIG. 1 is a block diagram illustrating a configuration example of an embodiment of an endoscope system according to the present technology.

The endoscope system in FIG. 1 is configured by an endoscope camera head 11, a camera control unit (CCU) 12, an operation section 13, and a display 14.

This endoscope system is used in endoscopic surgery in which a region (surgery region) in a body being a surgical target is captured as an observed portion and is displayed on the display 14, and the observed portion is treated while viewing the display 14.

Figure 2:
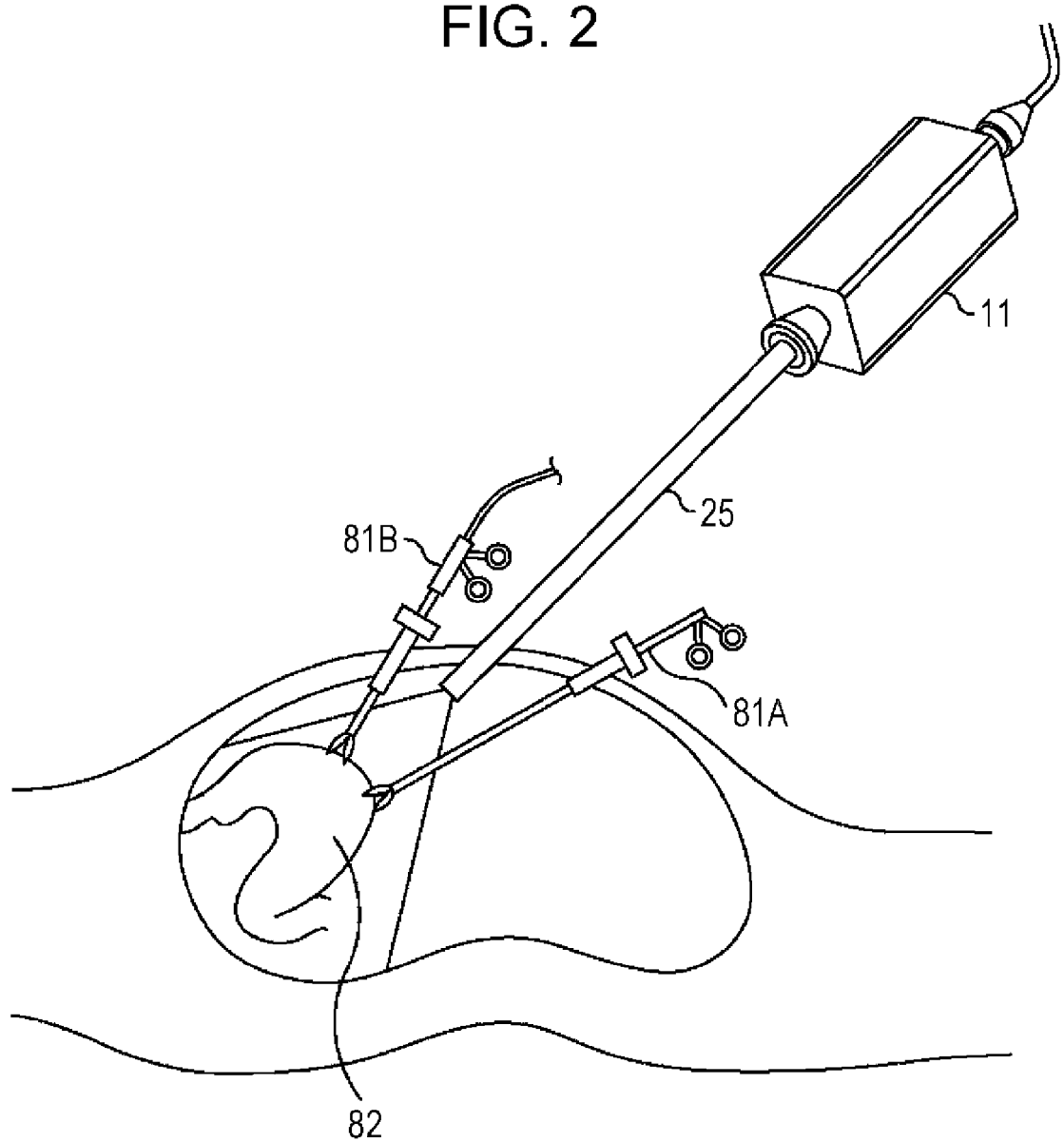
FIG. 2 is a diagram illustrating a usage state of the endoscope system.

In the endoscopic surgery, for example, as illustrated in FIG. 2, an insertion portion 25 of the endoscope camera head 11 and two pairs of forceps 81 (81A and 81B) being surgical instruments are inserted into the body of a patient. The endoscope camera head 11 emits light from a tip end of the insertion portion 25, illuminates a surgery region 82 of the patient, and images a state of the two pairs of forceps 81 and the surgery region 82.

Here, an endoscope will be described as an example, but the present technology may be also applied to an apparatus other than a medical apparatus such as an endoscope. For example, the present technology may be applied to an apparatus of executing some types of processes on a remarkable region corresponding to a surgery region by an instructing tool, a predetermined device, or the like corresponding to the surgical instrument.

The endoscope camera head 11 includes an imaging section 21, a light source 22, and a focus lens 23, as illustrated in FIG. 1.

The imaging section 21 includes at least two imaging sensors 24 of a first imaging sensor 24a and a second imaging sensor 24b. The imaging sensor 24 is configured by, for example, a charge coupled device (CCD) sensor, a complementary metal oxide semiconductor (CMOS) sensor, or the like. The imaging sensor 24 images a subject and generates an image obtained as a result. The imaging sensor 24 may employ a high resolution sensor which has the number of pixels of about 4000×about 2000 being the number of pixels of (horizontal direction)×(vertical direction) and is called a 4K camera. The two imaging sensors 24 are disposed at a predetermined distance from each other in a traverse direction and generate images having view point directions different from each other to output the images to the CCU 12.

In this embodiment, images obtained by the two imaging sensors 24 performing imaging are referred to as surgery region images. In this embodiment, the first imaging sensor 24a is set to be disposed on a right side and the second imaging sensor 24b is set to be disposed on a left side, and the surgery region image generated by the first imaging sensor 24a is referred to as an R image and the surgery region image generated by the second imaging sensor 24b is referred to as an L image.

The light source 22 is configured by, for example, a halogen lamp, a xenon lamp, a light emitting diode (LED) light source, and the like and the light source 22 emits light for illuminating the surgery region.

The focus lens 23 is configured by one or a plurality of lenses, and is driven by a focus control section 46 (will be described later) of the CCU 12 and forms an image on an imaging surface of the imaging sensor 24 by using incident light (image light) from the subject.

The CCU 12 is an image processing apparatus for processing the surgery region image obtained by the imaging section 21 of the endoscope camera head 11 performing imaging. The CCU 12 is configured by a depth information generation section 41, a forceps position detection section 42, a remarkable point estimation section 43, an image superposition section 44, an operation control section 45, and a focus control section 46.

An R image and an L image which are generated and output in the imaging section 21 are supplied to the depth information generation section 41 and the image superposition section 44 of the CCU 12. One (for example, L image) of the R image and the L image is also supplied to the focus control section 46.

The depth information generation section 41 generates depth information of the surgery region image from the supplied R image and L image. More specifically, the depth information generation section 41 calculates a position of each pixel of the surgery region image in a depth direction by using the supplied R image and L image and a principle of triangulation.

A calculation method of a depth position of each pixel in the surgery region image will be described by using the principle of triangulation with reference to FIG. 3 and FIG. 4.

Figure 3:
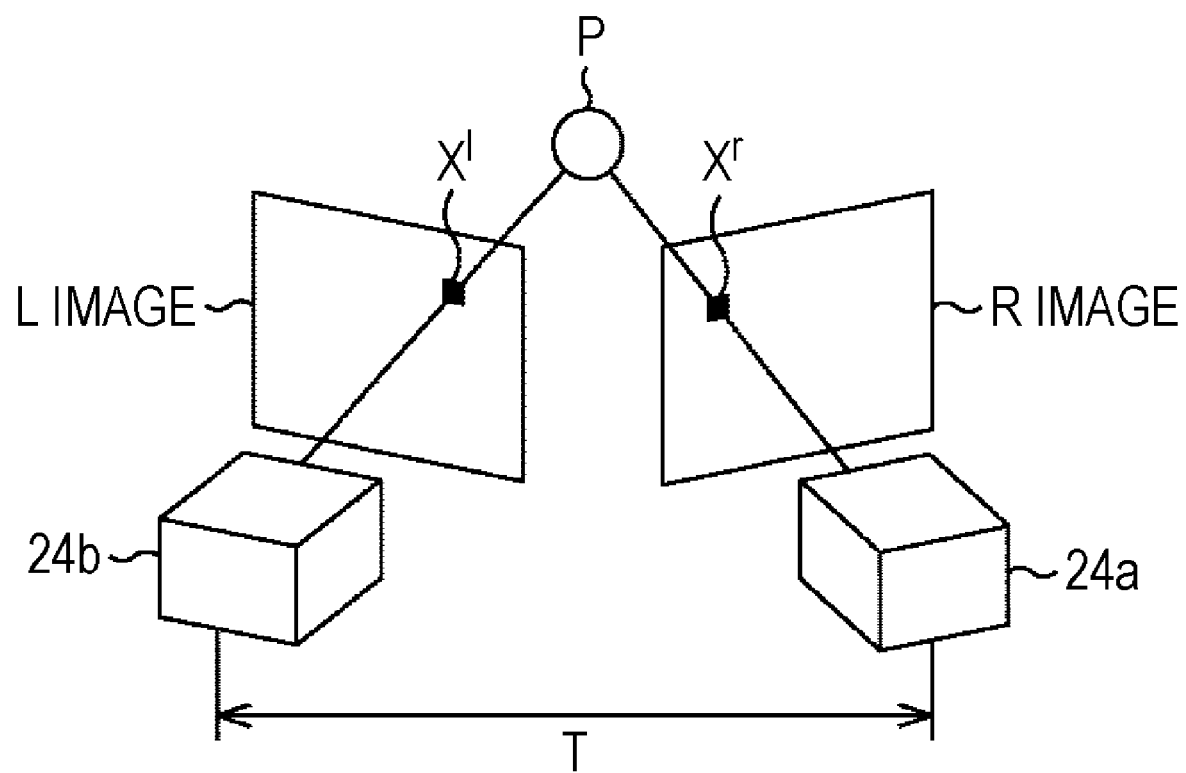
FIG. 3 is a diagram illustrating a calculation method of a depth position.

First, the first imaging sensor 24a and the second imaging sensor 24b are arranged in a row at a distance T in the traverse direction, as illustrated in FIG. 3, and each of the first imaging sensor 24a and the second imaging sensor 24b images an object P in the real world.

The positions of the first imaging sensor 24a and the second imaging sensor 24b in the vertical direction are the same as each other and the positions in the horizontal direction are different from each other. Thus, the position of the object P in the R image obtained by the first imaging sensor 24a and the position of the object P in the L image obtained by the second imaging sensor 24b are different only in x coordinates.

For example, the x coordinate of the object P shown in the R image obtained by the first imaging sensor 24a is set to $x^r$ and the x coordinate of the object P shown in the L image obtained by the second imaging sensor 24b is set to $x^l$.

If the principle of triangulation is used, as illustrated in FIG. 4, the x coordinate of the object P in the R image being $x^r$ corresponds to a position on a straight line joining an optical center $O_r$ of the first imaging sensor 24a and the object P. The x coordinate of the object P in the L image being $x^l$ corresponds to a position on a straight line joining an optical center $O_l$ of the second imaging sensor 24b and the object P.

Here, when a distance from the optical center $O_r$ to an image plane of the R image or from the optical center $O_l$ to an image plane of the L image is set as f and a distance (depth) from the a line joining the optical center $O_r$ and the optical center $O_l$ to the object P in the real world is set as Z, parallax d is represented by $d=(x^l-x^r)$.

A relationship of the Equation (1) is established between T, Z, d, and f.

[Math. 1]

$$\frac{T-d}{Z-f} = \frac{T}{Z} \quad (1)$$

Accordingly, the distance Z to the object P may be obtained by using the following Equation (2) which is obtained by deforming the Equation (1).

[Math. 2]

$$Z = \frac{fT}{x^l - x^r} \quad (2)$$

The depth information generation section 41 in FIG. 1 calculates a depth Z of each pixel in the surgery region image by using the above-described principle of the triangulation. The depth Z of each pixel calculated by the depth information generation section 41 is supplied to the forceps position detection section 42 and the remarkable point estimation section 43, as depth information.

The forceps position detection section 42 detects a position of an important object such as the forceps 81 shown in the surgery region image using the depth information of the surgery region image supplied from the depth information generation section 41. As described above, the two pairs of forceps 81 may be imaged as subjects in the surgery region image. However, a position of either of the forceps 81 may be detected. The position of the distal end of the forceps 81 may also be detected. The forceps 81 of which the position is to be detected may be determined in advance or the forceps of which the position is detected more easily than another in the surgery region image may be determined. In addition, the positions of the two pairs of forceps 81 may also be detected.

Position detection of the forceps 81 performed by the forceps position detection section 42 will be described with reference to FIG. 5A to FIG. 5D.

First, the forceps position detection section 42 generates a parallax image from depth information of the surgery region image supplied from the depth information generation section 41. The parallax image refers to an image obtained by representing the depth Z of each pixel being the depth information, in gray scale.

FIG. 5A illustrates an example of the parallax image and represents that brightness value in the parallax image becomes greater, corresponding depth Z becomes less, and the subject in the surgery region image becomes closer to the front.

Then, the forceps position detection section 42 detects an edge which is a boundary between brightness values, from the generated parallax image. For example, pixels which have a difference between pixel values of adjacent pixels is equal to or greater than a predetermined value in the parallax image are detected as an edge. Alternatively, the forceps position detection section 42 may detect be detected from one or more of color difference information, brightness, and depth independent from or in concert with edge detection techniques.

An edge detection component is detected based on the brightness value. However, for example, the surgical field has red as a main component and the forceps has a color such as silver, white, and black different from red in general. Since the surgical field and the forceps have different colors as described above, edge detection based on color component information may be also performed. That is, a configuration in which a three-dimensional position of the surgical instrument such as forceps is detected based on information on a specific color in the parallax image may be made.

Figure 5B:
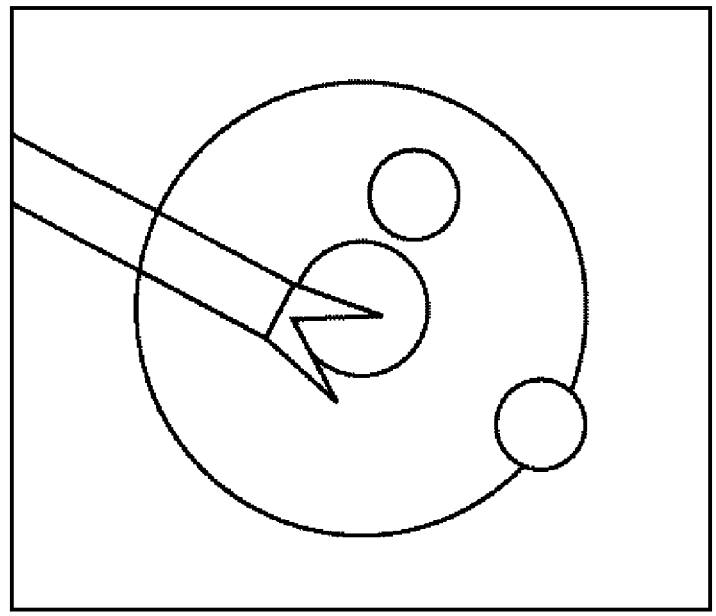
FIG. 5B is a diagram illustrating detection of the position of forceps.
Figure 5C:
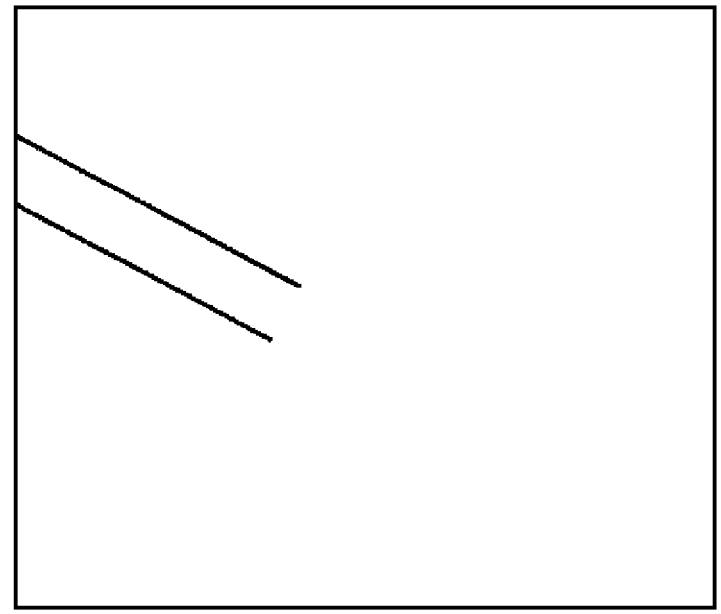
FIG. 5C is a diagram illustrating detection of the position of forceps.

Here, a case of using the brightness value will be described as an example. FIG. 5B illustrates an example of edges detected in the parallax image of FIG. 5A.

Then, the forceps position detection section 42 removes a curved edge out of the detected edge and detects only a linear edge having a predetermined length or greater.

Since the forceps 81 has a bar shape, there is the linear edge having a predetermined length or greater, as the edge of the forceps 81. Thus, the forceps position detection section 42 only detects the linear edge having a predetermined length or greater out of the detected edge as the edge of the forceps 81.

The forceps position detection section 42 may determine whether or not the detected linear edge is a straight line continuing from an outer circumference portion of the surgery region image in addition to determining whether or not the detected linear edge has the predetermined length or greater, when the edge of the forceps 81 is specified. When the insertion portion 25 of the endoscope camera head 11 and the forceps 81 have a position relationship as illustrated in FIG. 2, the forceps 81 generally is captured to have a position of being extended to a center portion from the outer circumference portion of the surgery region image in the surgery region image. For this reason, it is possible to further raise detection accuracy of the forceps 81 by determining whether or not the detected linear edge is a straight line continuing from the outer circumference portion of the surgery region image.

Then, the forceps position detection section 42 estimates a position of the forceps 81 in the three-dimensional space in the captured image, that is, a posture of the forceps 81, from the detected linear edge.

Figure 5D:
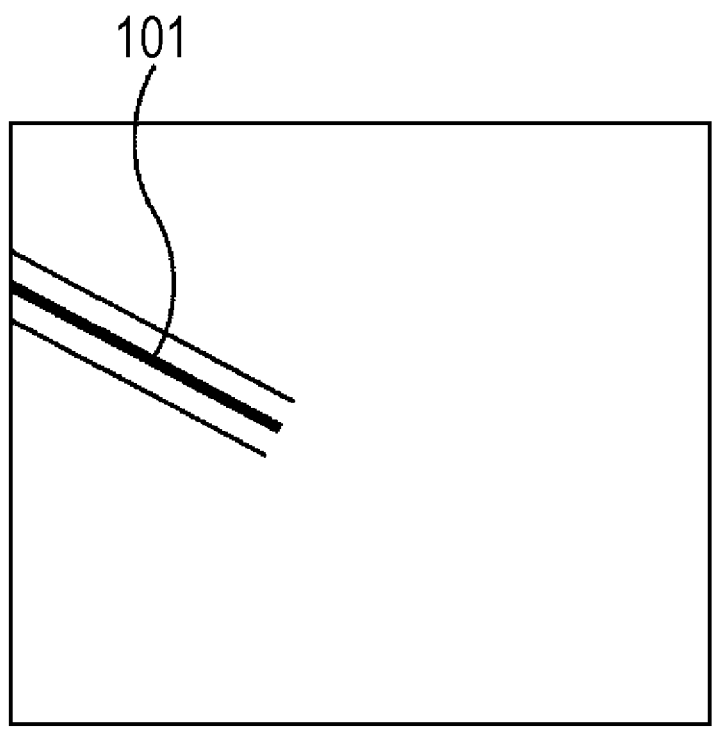
FIG. 5D is a diagram illustrating detection of the position of forceps.

Specifically, the forceps position detection section 42 calculates a line segment (straight line) 101 corresponding to the forceps 81, from the detected linear edge, as illustrated in FIG. 5D. The line segment 101 may be obtained by using an intermediate line between the detected two linear edges, and the like.

The forceps position detection section 42 arbitrarily detects two points $(x_1, y_1)$ and $(x_2, y_2)$ on the calculated line segment 101 and acquires depth positions $z_1$ and $z_2$ at positions $(x_1, y_1)$ and $(x_2, y_2)$ of the detected two points from the supplied depth information. Accordingly, the positions $(x_1, y_1, z_1)$ and $(x_2, y_2, z_2)$ of the forceps 81 in the three-dimensional space are specified in the surgery region image. The positions may include, for example, the distal end of the forceps.

When two line segments corresponding to two pairs of forceps 81 are detected in the surgery region image, either of the two line segments may be selected by selecting one closer to the front than another.

Returning to FIG. 1, the forceps position detection section 42 supplies the positions $(x_1, y_1, z_1)$ and $(x_2, y_2, z_2)$ of the forceps 81 in the three-dimensional space which are detected in the above-described manner, to the remarkable point estimation section 43.

The depth information of the surgery region image is supplied from the depth information generation section 41 to the remarkable point estimation section 43 and the coordinates $(x_1, y_1, z_1)$ and $(x_2, y_2, z_2)$ of the two points in the three-dimensional space which represent a posture of the forceps 81 are supplied from the forceps position detection section 42 to the remarkable point estimation section 43.

Alternatively to the forceps position detection section 42, element 42 can also be an area position detection section. The area position detection section 42 detects an important area having, for example, certain tissues, body parts, bleeding or blood vessels, etc. The detection of the important area is based on color information, brightness and/or differences between different frames. For example, an important area could be detected as an area having no bleeding in one frame and then bleeding in subsequent frames.

Figure 6:
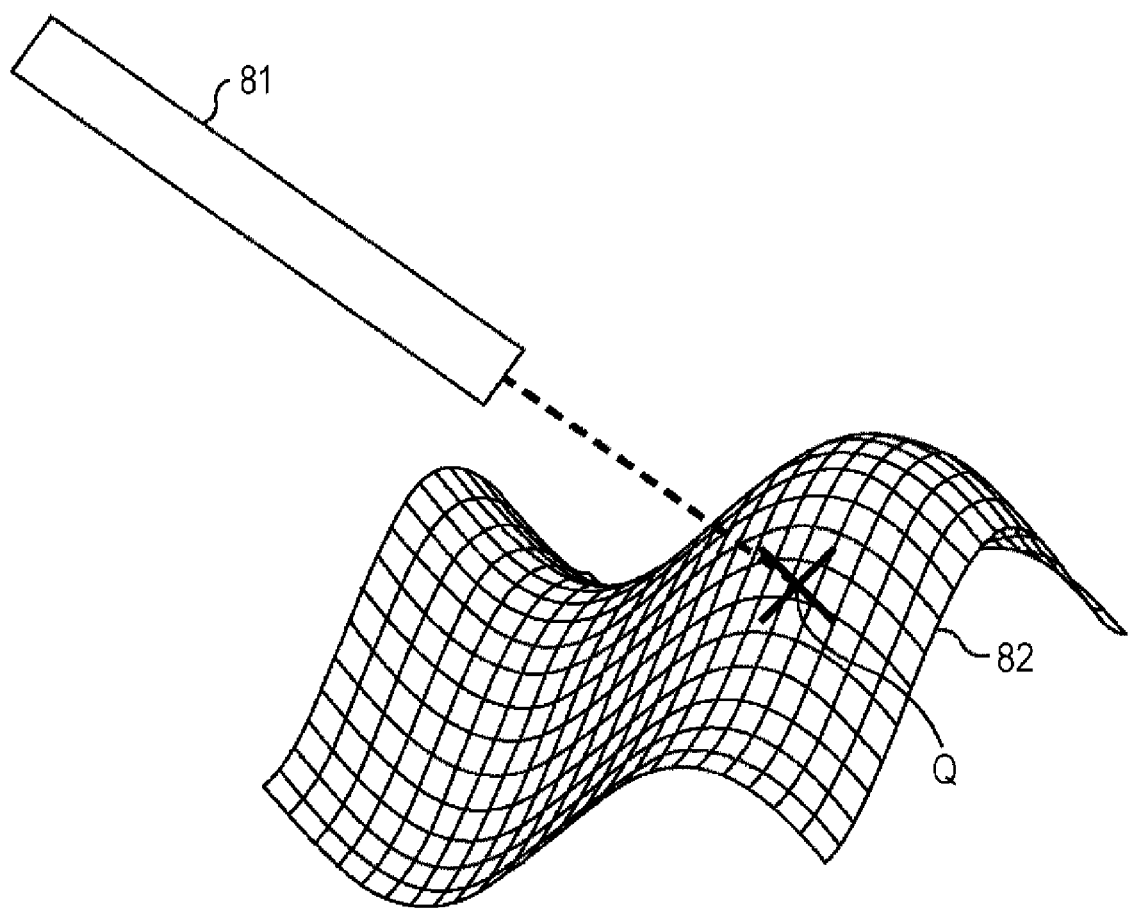
FIG. 6 is a diagram illustrating detection of a position of a remarkable point.

The remarkable point estimation section 43 assumes that a remarkable point Q at the surgery region 82 is at a position obtained by extending the detected positions of the forceps 81 and estimates a position of the remarkable point Q of the surgery region 82 in the three-dimensional space, as illustrated in FIG. 6. The remarkable point Q at the surgery region 82 corresponds to an intersection point of an extension line obtained by extending the detected posture of the forceps 81 and a surface of the surgery region 82. An estimated location coordinate of the remarkable point Q at the surgery region 82 in the three-dimensional space is supplied to the image superposition section 44.

The remarkable point estimation section 43 can also estimate the remarkable point Q from the determined important area. In particular, the remarkable point Q can be generated based on the position of the important area.

The image superposition section 44 generates a superposition image by superposing a predetermined mark (for example, a mark of x), a circle or a quadrangle as the region of interest having a predetermined size in which the remarkable point Q supplied from the remarkable point estimation section 43 is set as the center on a position at which the remarkable point Q of the surgery region image supplied from the imaging section 21 is set as the center and the image superposition section 44 displays the generated superposition image on the display 14.

A configuration in which display mode information which is control information for designating ON or OFF of the 3D display is supplied to the image superposition section 44 from the operation control section 45 may be also made. The image superposition section 44 supplies any one of the R image and the L image to the display 14 and causes the surgery region image to be displayed in the 2D display manner when OFF of the 3D display is designated through the display mode information.

On the other hand, when an instruction of ON of the 3D display is received through the display mode information, the image superposition section 44 supplies both of the R image and the L image to the display 14 and causes the surgery region image to be displayed in a 3D manner. Here, the 3D display refers to an image display manner in which the R image and the L image are alternately displayed on the display 14, the right eye of a practitioner visually recognizes the R image, the left eye of the practitioner visually recognizes the L image, and thus the practitioner perceives the surgery region image three-dimensionally.

The operation control section 45 supplies various control signals to necessary sections based on an operation signal supplied from the operation section 13. For example, the operation control section 45 supplies an instruction of focus matching to the focus control section 46 in accordance with an instruction of matching a focus with an area including the remarkable point Q generated in the operation section 13.

The focus control section 46 performs focus control by using a contrast method, based on the L image supplied from the imaging section 21. Specifically, the focus control section 46 drives the focus lens 23 of the endoscope camera head 11 and compares contrast of the L image supplied from the imaging section 21 to detect a focus position. The focus control section 46 may perform the focus control in which the location coordinate of the remarkable point Q is acquired from the remarkable point estimation section 43 and an area of a predetermined range having the remarkable point Q as the center is set to be a focus control target area.

The operation section 13 includes at least a foot pedal 61. The operation section 13 receives an operation from a practitioner (operator) and supplies an operation signal corresponding to an operation performed by the practitioner to the operation control section 45. The practitioner may perform, for example, matching a focus with a position of the mark indicating the remarkable point Q displayed on the display 14, switching the 2D display and the 3D display of the surgery region image displayed on the display 14, setting zoom magnification of the endoscope, and the like by operating the operation section 13.

The display 14 is configured by, for example, a liquid crystal display (LCD) and the like and displays a surgery region image captured by the imaging section 21 of the endoscope camera head 11 based on an image signal supplied from the image superposition section 44. When the superposition mode is set to be ON, a surgery region image captured by the imaging section 21 or a superposition image obtained by superposing a mark which has a predetermined shape and indicates a position of the remarkable point Q estimated by the remarkable point estimation section 43 on the surgery region image is displayed on the display 14.

Figure 7:
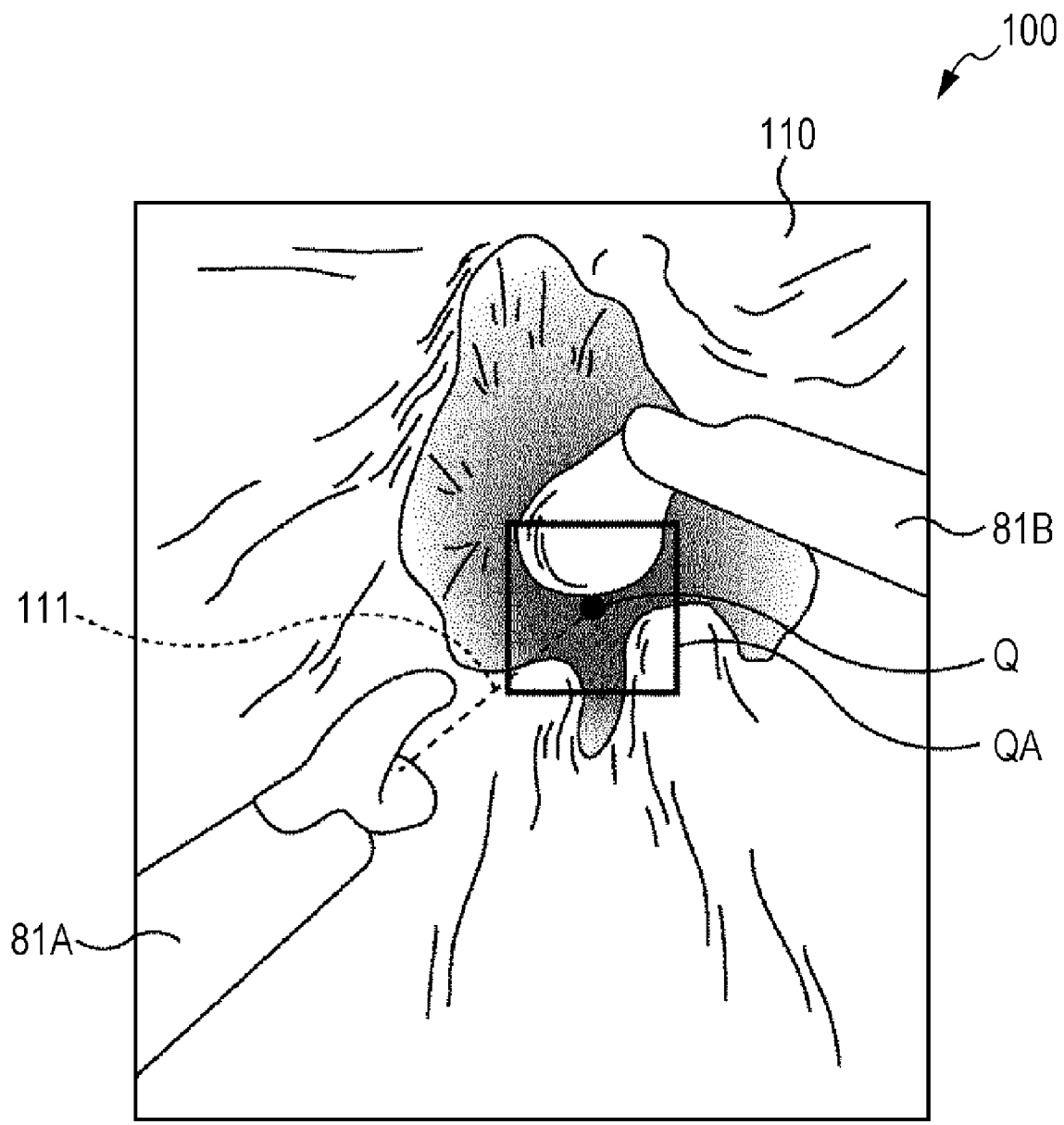
FIG. 7 is a diagram illustrating an example of a superposition image to be displayed on a display.

FIG. 7 illustrates an example of the superposition image displayed on the display 14.

In a superposition image 100 of FIG. 7, an area of interest (region of interest) QA which is determined to be an area including the remarkable point Q and has a predetermined size is indicated on a surgery region image 110 supplied from the imaging section 21 by a quadrangular mark.

In the surgery region image 110, the two pairs of forceps 81A and 81B are imaged and the remarkable point Q is estimated based on a position of the forceps 81A on the left side. In the superposition image 100, the estimated remarkable point Q, the mark (quadrangle indicating the area of interest in FIG. 7) for causing the practitioner to recognize the remarkable point Q, and a guide line 111 corresponding to an extension line calculated through estimation of the remarkable point Q are displayed. The area of interest (region of interest) QA may be overlapping on or adjacent to and/or distinct from the region including the forceps 81 or the important area.

In a configuration in which the guide line 111 is displayed, display of the guide line 111 allows a three-dimensional distance in the abdominal cavity to be recognized intuitively and may cause three-dimensional distance information to be provided for the practitioner in a plan view.

In FIG. 7, the quadrangle is illustrated as a mark or highlight for causing the practitioner to recognize the remarkable point Q, but the mark is not limited to the quadrangle. As the mark, other shapes such as a triangle may be applied. In addition, a mark of a shape such as an (x) mark may be displayed.

<Flow of Focusing Process>

Then, in the endoscope system of FIG. 1, a process when a remarkable point Q is detected and a focus is matched with a position of the remarkable point Q will be described with reference to a flowchart of FIG. 8. Whether or not such a process (process of auto-focusing) of detecting a remarkable point Q and performing matching of a focus is executed may be set by a practitioner. A configuration in which a process of the flowchart illustrated in FIG. 8 is executed when auto-focusing is set to be executed may be made.

In addition, a configuration in which setting whether or not auto-focusing is executed is performed by operating the foot pedal 61 may be made.

Figure 8:
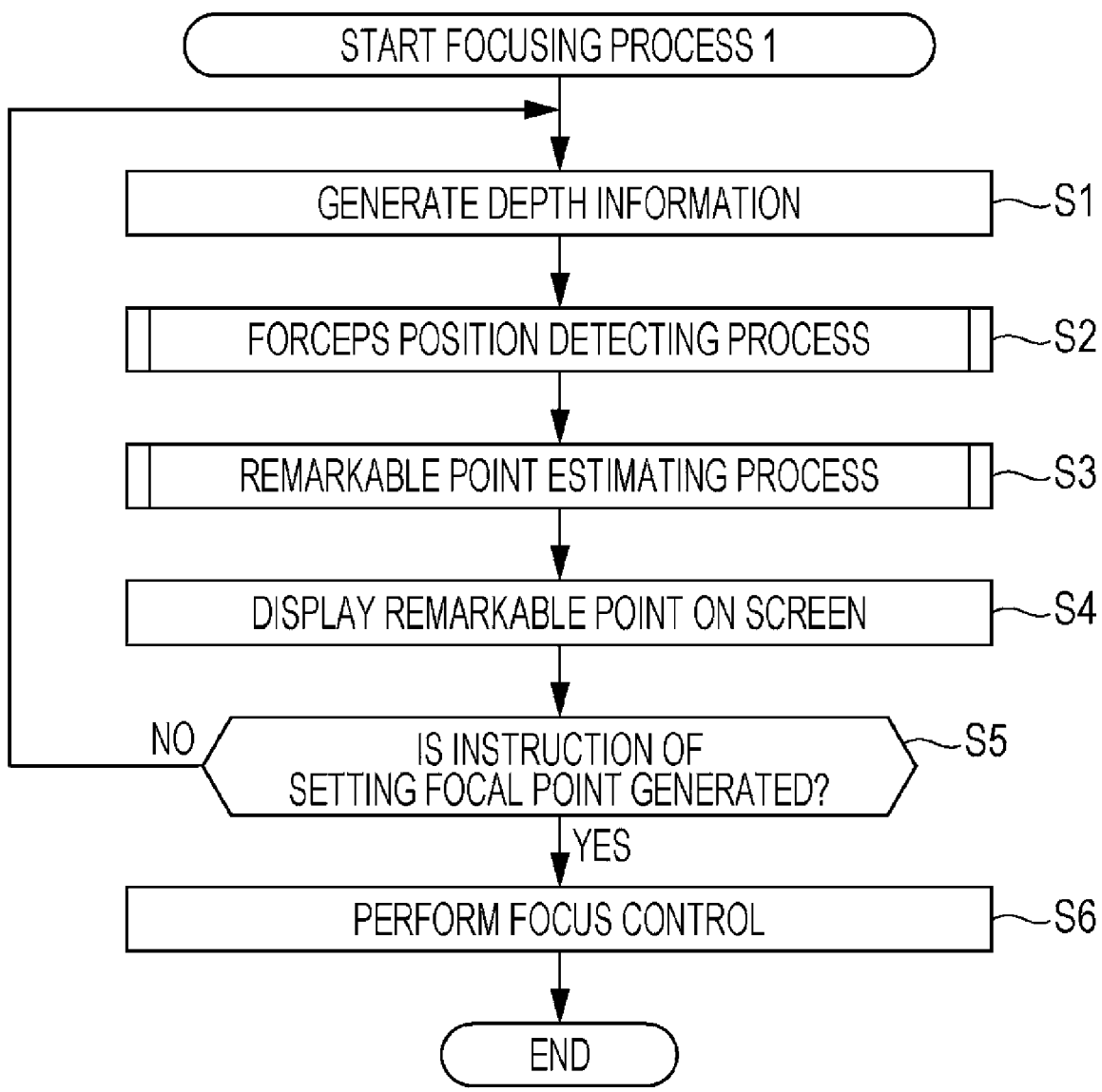
FIG. 8 is a flowchart illustrating focus control.

A configuration in which a process based on the flow of the focusing process illustrated in FIG. 8 is started when a practitioner operates a start button (the foot pedal 61 is available), when an optical zoom and the like is determined to be out of focus, and the like may be made. The present technology may be also applied to a microscope system and have a configuration in which the process based on the flow of the focusing process illustrated in FIG. 8 is started using movement of an arm as a trigger in the microscope system.

FIG. 8 illustrates the flowchart of the focusing process. Power is supplied to each mechanism of the endoscope system in a state where the focusing process of FIG. 8 is executed. The insertion portion 25 of the endoscope camera head 11 and the forceps 81 are inserted into the body of a patient and the light source 22 illuminates the surgery region 82 of the patient.

First, in Step S1, the depth information generation section 41 generates depth information of a surgery region image from an R image and an L image supplied from the imaging section 21 of the endoscope camera head 11. More specifically, the depth information generation section 41 calculates depth Z of the each location (pixel) in the surgery region image by using the Equation (2) which uses the principle of triangulation described with reference to FIG. 4. Depth information calculated in the depth information generation section 41 is supplied to the remarkable point estimation section 43 and the forceps position detection section 42.

A process of Step S1 is a process for determining three-dimensional positions of a surface of a subject imaged by the imaging section 21.

In Step S2, the forceps position detection section 42 executes a forceps position detecting process of detecting a position of the forceps 81 in the surgery region image using the depth information of the surgery region image supplied from the depth information generation section 41. A process of Step S2 is a process for detecting a three-dimensional position of a bar shaped instrument such as forceps held by a practitioner. Step S2 can alternatively correspond to the area position detection section 42 executing an area position detecting process.

<Detailed Flow of Forceps Position Detecting Process>

Figure 9:
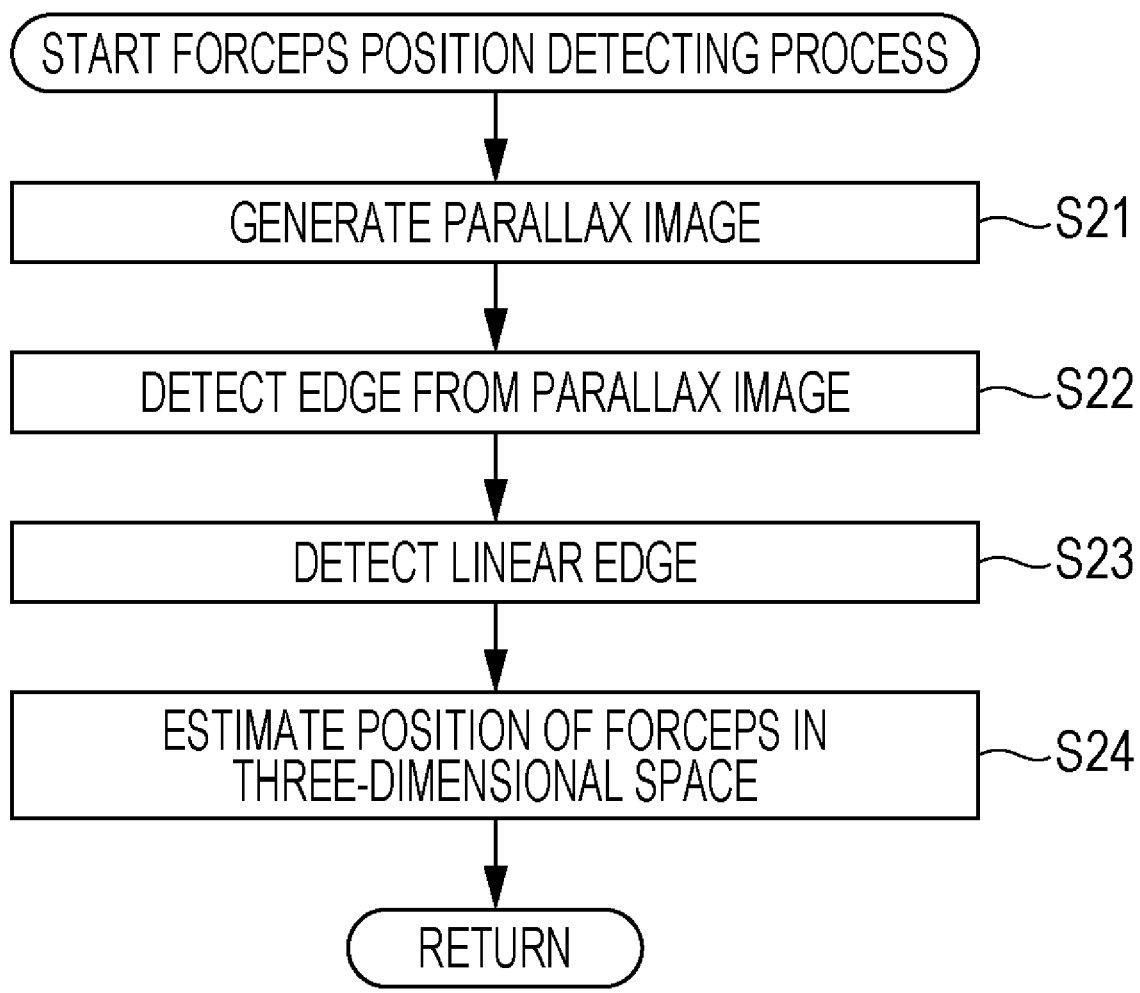
FIG. 9 is a flowchart illustrating a forceps position detecting process in detail.

FIG. 9 illustrates a detailed flowchart of the forceps position detecting process executed in Step S2.

In the forceps position detecting process, at first, in Step S21, the forceps position detection section 42 generates a parallax image from the depth information of the surgery region image supplied from the depth information generation section 41.

In Step S22, the forceps position detection section 42 detects an edge which is a boundary between brightness values from the generated parallax image.

In Step S23, the forceps position detection section 42 removes a curved edge out of the detected edge and detects only a linear edge having a predetermined length or greater.

In Step S24, the forceps position detection section 42 estimates a position of the forceps 81 in the surgery region image in the three-dimensional space from the detected linear edge. With this, as described above with reference to FIG. 5D, coordinates $(x_1, y_1, z_1)$ and $(x_2, y_2, z_2)$ of two points indicating positions of the forceps 81 in the surgery region image in the three-dimensional space are determined. The positions may be for example the distal end of the forceps.

The positions $(x_1, y_1, z_1)$ and $(x_2, y_2, z_2)$ of the forceps 81 in the surgery region image, which are detected as described above, are supplied to the remarkable point estimation section 43 and the process proceeds to Step S3 in FIG. 8.

In Step S3, the remarkable point estimation section 43 executes a remarkable point estimating process of assuming that a remarkable point Q at the surgery region 82 is at a position obtained by extending the detected positions of the forceps 81 and of detecting a position of the remarkable point Q of the surgery region 82 in the three-dimensional space.

<Detailed Flow of Remarkable Point Estimating Process>

Figure 10:
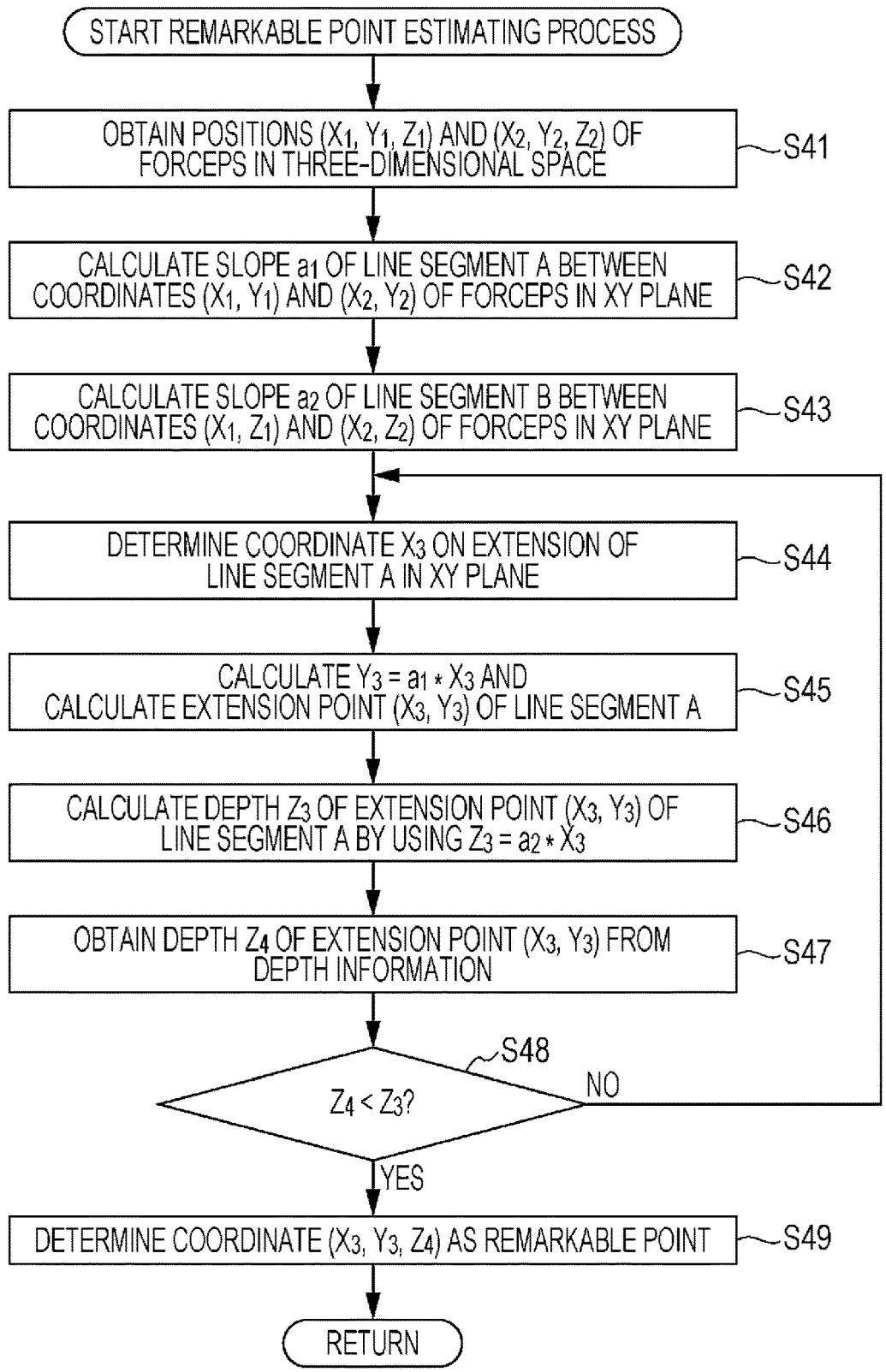
FIG. 10 is a flowchart illustrating a remarkable point estimating process in detail.

The remarkable point estimating process executed in Step S3 of FIG. 8 will be described in detail with reference to a flowchart of FIG. 10.

First, in Step S41, the remarkable point estimation section 43 obtains positions $(x_1, y_1, z_1)$ and $(x_2, y_2, z_2)$ of the forceps 81 in the surgery region image in the three-dimensional space which are supplied from the forceps position detection section 42.

In Step S42, the remarkable point estimation section 43 calculates a slope $a_1$ of a line segment A joining the coordinates $(x_1, y_1)$ and $(x_2, y_2)$ of the two points of the forceps in an XY plane. The slope $a_1$ may be calculated by using the following equation.

$$a_1 = (Y_2 - Y_1)/(X_2 - X_1)$$

In Step S43, the remarkable point estimation section 43 calculates a slope $a_2$ of a line segment B joining the coordinates $(X_1, Z_1)$ and $(X_2, Z_2)$ of the two points of the forceps in an XZ plane. The slope $a_2$ may be calculated by using the following equation.

$$a_2 (Z_2 - Z_1)/(X_2 - X_1)$$

In Step S44, the remarkable point estimation section 43 determines a coordinate $X_3$ being an X coordinate value when the line segment A in the XY plane is extended by a predetermined length W in a center direction of the screen. The predetermined length W can be defined as 1/N (N is a positive integer) of the line segment A, for example.

In Step S45, the remarkable point estimation section 43 calculates $Y_3=a_1*X_3$ and calculates an extension point $(X_3, Y_3)$ of the line segment A in the XY plane. Here, "*" represents multiplication.

In Step S46, the remarkable point estimation section 43 calculates depth $Z_3$ of the extension point $(X_3,Y_3)$ of the line segment A in the XZ plane by using $Z_3=a_2*X_3$. Here, the calculated depth $Z_3$ of the extension point $(X_3, Y_3)$ of the line segment A in the XZ plane corresponds to a logical value of the extension point $(X_3, Y_3)$.

In Step S47, the remarkable point estimation section 43 acquires depth $Z_4$ of the extension point $(X_3, Y_3)$ of the line segment A from the depth information supplied from the depth information generation section 41. Here, the acquired depth $Z_4$ of the extension point $(X_3, Y_3)$ corresponds to a real value of the extension point $(X_3, Y_3)$.

In Step S48, the remarkable point estimation section 43 determines whether or not the depth $Z_3$ being the logical value of the extension point $(X_3, Y_3)$ is greater than the depth $Z_4$ being the real value of the extension point $(X_3, Y_3)$.

A case where the extension point $(X_3, Y_3)$ obtained by extending the line segment A which corresponds to the forceps 81 by the predetermined length W in the center direction of the screen is not included in the surgery region 82 means a case where the surgery region 82 is at a position deeper than the extension point $(X_3, Y_3)$. In this case, the depth $Z_4$ being the real value of the extension point $(X_3, Y_3)$ obtained from the depth information is greater than the depth $Z_3$ being the logical value.

On the other hand, when the surgery region 82 actually includes the extension point $(X_3, Y_3)$, the real value (depth $Z_4$) of the extension point $(X_3, Y_3)$ obtained from the depth information becomes ahead of the logical value (depth $Z_3$) of the extension point $(X_3, Y_3)$. Thus, the depth $Z_4$ being the real value of the extension point $(X_3, Y_3)$ is less than the depth $Z_3$ being the logical value.

Accordingly, in Step S48, the remarkable point estimation section 43 determines whether or not the logical value (depth $Z_3$) of the extension point $(X_3, Y_3)$ obtained by extending the line segment A by the predetermined length W becomes ahead of the real value (depth $Z_4$) of the extension point $(X_3, Y_3)$ obtained from the depth information.

In Step S48, when the depth $Z_3$ being the logical value of the extension point $(X_3, Y_3)$ is equal to or less than the depth $Z_4$ being the real value of the extension point $(X_3,Y_3)$, that is, when the depth $Z_3$ being the logical value of the extension point $(X_3, Y_3)$ is determined to be ahead of the depth $Z_4$ being the real value of the extension point $(X_3, Y_3)$, the process returns to Step S44.

In Step S44 to which the process returns, a coordinate $X_3$ obtained by extending the line segment A in the center direction of the screen to be deeper than the current extension point $(X_3, Y_3)$ by the predetermined length W in the XY plane is determined as a new coordinate $X_3$. Steps S45 to S48 which are described above are executed again on the determined new coordinate $X_3$.

On the other hand, in Step S48, when the depth $Z_3$ being the logical value of the extension point $(X_3, Y_3)$ is greater than the depth $Z_4$ being the real value, that is, when the depth $Z_4$ being the real value of the extension point $(X_3, Y_3)$ is determined to be ahead of the depth $Z_3$ being the logical value, the process proceeds to Step S49.

In Step S49, the remarkable point estimation section 43 determines an extension point $(X_3, Y_3, Z_4)$ which has the depth $Z_4$ being the real value as a Z coordinate value to be the remarkable point Q.

In this manner, Step S3 of FIG. 8 is completed and the process proceeds to Step S4.

In Step S4, the estimated (detected) remarkable point Q is displayed on a screen. For example, a predetermined mark is displayed at the position of the remarkable point Q, as described with reference to FIG. 7.

In Step S5, it is determined whether or not an instruction of setting a focal point is generated. The practitioner operates the foot pedal 61 of the operation section 13 when the practitioner wishes to control the remarkable point Q displayed on the display 14 to be a focal point. When such this operation is performed, it is determined that the instruction of controlling the estimated remarkable point to be focal point is generated.

Here, it is described that operating the foot pedal 61 causes an instruction of setting a focal point. However, for example, a configuration will be made in which an instruction of setting a focal point is generated using other methods such as a method in which a switch (not illustrated) attached to the forceps is operated and a method in which a word preset through voice recognition is spoken.

In Step S5, when it is determined that the instruction of setting a focal point is not generated, the process returns to Step S1 and the subsequent processes are repeated.

On the other hand, in Step S5, when it is determined that the instruction of setting a focal point is generated, the process proceeds to Step S6 and the focus control section 46 performs the focus control. The focus control section 46 performs the focus control in such a manner that the focus control section 46 obtains information on a coordinate position and the like of the remarkable point estimated by the remarkable point estimation section 43 and sets a focus to match with the position of the remarkable point Q with the obtained information by, for example, the above-described contrast method.

Meanwhile, when it is determined that the instruction of setting a focal point is not generated in Step S5, as illustrated in FIG. 8, the process returns to Step S1, depth information is generated again, and the subsequent processes are repeated in a case where three-dimensional positions of the surface of the imaged subject may be changed due to movement of the endoscope camera head 11.

The present technology may be applied to a microscope system other than the above-described endoscope system, similarly. In this case, a microscope camera head may be provided instead of the endoscope camera head 11 in FIG. 1 and the CCU 12 may execute a superposition displaying process of the surgery region image imaged by the microscope camera head.

In the microscope system, a configuration in which when the instruction of setting a focal point is not generated in Step S5 illustrated in FIG. 8, the process returns to Step S2 and the subsequent processes are repeated may be made in a case where the microscope camera head and the subject are fixed and thus it is unlikely that the three-dimensional positions of the surface of the subject imaged by the imaging section 21 are changed. In this case, the three-dimensional positions (depth information) of the surface of the imaged subject are obtained once at first and then the processes are executed by repeatedly using the obtained depth information.

For example, depth information may be also generated in Step S1 for each predetermined period and the generated depth information may be updated in a configuration in which the process returns to Step S2 and the subsequent processes are repeated when it is determined that the instruction of setting a focal point is not generated in Step S5.

In the above-described forceps position detecting process, an example in which the forceps 81 is detected by generating a parallax image from the depth information of the surgery region image and detecting a linear edge will be described. However, other detecting methods may be employed.

For example, marks may be marked on two predetermined locations of the forceps 81 and the two marks marked on the forceps 81 may be detected as positions $(x_1,y_1,z_1)$ and $(x_2,y_2,z_2)$ of the forceps 81 in the surgery region image. Characteristics such as a shape and a color of the forceps 81, and a shape and a color of the mark marked on the forceps 81 of various forceps 81 used in performing surgery are stored in advance in a memory of the forceps position detection section 42 as a database and the mark may be detected based on information on the designated forceps 81.

In this manner, since a direction pointed by the forceps is a direction on which the practitioner focuses and a focus is controlled to match with a portion of the subject image positioned in the direction, the practitioner may make a focus match with a desired portion without separating the practitioner from the instrument such as the forceps. Accordingly, it is possible to provide an endoscope system or a microscope system having good convenience and improved operability.

<The Other Flow of Focusing Process>

Other process according to the focus control of the endoscope system will be described with reference to a flowchart illustrated in FIG. 11.

In Step S101, the forceps position detection section 42 executes the forceps position detecting process of detecting a position of the forceps 81 in the surgery region image. The process in Step S101 corresponds to a process for detecting a three-dimensional position of a bar shaped instrument such as a forceps held by the practitioner. The forceps position detecting process in Step S101 may be executed similarly to the process of Step S2 illustrated in FIG. 8.

In Step S102, the depth information generation section 41 generates depth information of the surgery region image from an L image and an R image supplied from the imaging section 21 of the endoscope camera head 11. A process of Step S102 corresponds to a process for determining three-dimensional positions of the surface of the subject imaged by the imaging section 21. The forceps position detecting process in Step S102 may be executed similarly to the process of Step S1 illustrated in FIG. 8.

A process based on a flowchart illustrated in FIG. 11 is obtained by reversing an order of generating depth information and then detecting a position of the forceps in the process based on the flowchart illustrated in FIG. 8 and is executed in order of detecting the position of the forceps and then generating the depth information.

In detecting the position of the forceps, a portion which is on an extension of the tip end (distal end) portion of the forceps and overlapped with the subject image may be estimated. The process for generating the depth information is executed on the estimated portion of the subject image. That is, an area for generating depth information is extracted and the depth information in the extracted area is generated in the process of the flowchart illustrated in FIG. 11.

In this manner, it is possible to reduce processing capacity or processing time necessary for generating depth information by extracting an area for generating depth information.

Processes of Step S103 to Step S106 are executed similarly to the processes of Step S3 to Step S6 in the flowchart of FIG. 8. Thus, descriptions thereof are omitted.

As described above, according to the present technology, a focus may be matched with an image at a portion pointed by the forceps and thus it is possible to match a focus with a desired portion without separating an instrument such as the forceps held with the hand by the an operator from the hand. Accordingly, it is possible to improve operability of the endoscope system.

<Regarding Recording Medium>

An image process executed by the CCU 12 may be executed with hardware or software. When a series of processes are executed with software, a program constituting the software is installed on a computer. Here, the computer includes a computer obtained by combining dedicated hardware, a general personal computer allowed to perform various functions by installing various programs, and the like.

FIG. 12 is a block diagram illustrating a configuration example of hardware of a computer in which the CCU 12 executes an image process by using a program.

In the computer, a central processing unit (CPU) 201, a read only memory (ROM) 202, and a random access memory (RAM) 203 are connected to each other through a bus 204.

An input and output interface 205 is connected to the bus 204. An input section 206, an output section 207, a storage section 208, a communication section 209, and a drive 210 are connected to the input and output interface 205.

The input section 206 is configured by a keyboard, a mouse, a microphone, and the like. The output section 207 is configured by a display, a speaker, and the like. The storage section 208 is configured by a hard disk, a non-volatile memory, and the like. The communication section 209 is configured by a network interface and the like. The drive 210 drives a removable recording medium 211 such as a magnetic disk, an optical disc, a magneto-optical disk, and a semiconductor.

In the computer configured as described above, the CPU 201 executes the above-described series of processes by loading a program stored in the storage section 208 on the RAM 203 through the input and output interface 205 and the bus 204 and executing the loaded program, for example.

In the computer, the program may be installed on the storage section 208 through the input and output interface 205 by mounting the removable recording medium 211 on the drive 210. The program may be received in the communication section 209 through a wired or wireless transmission medium such as a local area network, the Internet, and satellite data broadcasting and may be installed on the storage section 208. In addition, the program may be installed on the ROM 202 or the storage section 208 in advance.

In this specification, the steps illustrated in the flowcharts may be executed in time series in the illustrated order. The steps may be executed not necessarily in time series, but in parallel or at a necessary timing, for example, when calling is performed, and the like.

In this specification, the system means a set of multiple constituents (apparatus, module (component), and the like) and it is not necessary that all of the constituents are in the same housing. Accordingly, the system includes a plurality of apparatuses which are stored in separate housings and connected to each other through a network and one apparatus in which a plurality of modules are stored in one housing.

The embodiment of the present technology is not limited to the above-described embodiment and may be changed variously without departing the gist of the present technology.

For example, an embodiment obtained by combining some or all of the above-described embodiments may be employed.

For example, the present technology may have a configuration of cloud computing in which one function is distributed by a plurality of apparatuses through a network and the plurality of apparatuses together process the function.

Each step illustrated in the above-described flowcharts may be executed in one apparatus or may be distributed and executed in a plurality of apparatuses.

Furthermore, when one step includes a plurality of processes, the plurality of processes included in the one step may be executed in one apparatus or may be distributed and executed in a plurality of apparatuses.

The effects described in this specification are only examples and are not limited thereto. There may be effects other than the effects described in this specification.

The present technology may have the following configurations.

(1)

A medical image processing apparatus, comprising:

a controller including circuitry configured to determine a position of a distal end of an important object within a medical image, estimate a region of interest within the medical image adjacent to a region including the important object based on the position of the distal end of the important object, and control display of the region of interest.

(2)

The medical image processing apparatus according to (1), wherein the medical image includes a surgical image of a body.

(3)

The medical image processing apparatus according to (1) to (2), wherein the region of interest within the medical image is distinct from the region including the important object.

(4)

The medical image processing apparatus according to (1) to (3), wherein the controller including the circuitry is configured to determine the position of the distal end of the important object within the medical image based on three dimensional position information of the important object.

(5)

The medical image processing apparatus according to (1) to (4), wherein the controller including the circuitry is configured to control display of the region of interest by displaying one or more of: a zoomed image corresponding to the region of interest, the medical image having focus on the region of interest, and the medical image in which the region of interest is highlighted.

(6)

The medical image processing apparatus according to (1) to (5), wherein the controller including the circuitry is configured to estimate the region of interest based on a three-dimensional posture of the important object.

(7)

The medical image processing apparatus according to (1) to (6), wherein the controller including the circuitry is configured to estimate the region of interest by detecting an estimated position of a cross point between an extension from the distal end of the important object and a surface of a body.

(8)

The medical image processing apparatus according to (1) to (7), wherein the controller including the circuitry is configured to determine the position of the distal end of the important object within the medical image by detecting the position of the distal end of the important object using one or more of color difference information, edge detection techniques, brightness, and depth.

(9)

A method for processing a medical image by a medical image processing apparatus including a controller including circuitry, the method comprising:

determining, using the circuitry, a position of a distal end of an important object within the medical image;

estimating, using the circuitry, a region of interest within the medical image adjacent to a region including the important object based on the position of the distal end of the important object; and controlling, using the circuitry, display of the region of interest.

(10)

A non-transitory computer readable medium having stored thereon a program that when executed by a computer causes the computer to implement a method for processing a medical image by a medical image apparatus including a controller including circuitry, the method comprising:

determining, using the circuitry, a position of a distal end of an important object within the medical image;

estimating, using the circuitry, a region of interest within the medical image adjacent to a region including the important object based on the position of the distal end of the important object; and controlling, using the circuitry, display of the region of interest.

(11)

A medical image processing system, comprising:

a medical imaging device that obtains a medical image;

a display device having a display area; and a controller including circuitry configured to determine a position of a distal end of an important object within the medical image obtained by the medical imaging device, estimate a region of interest within the medical image adjacent to a region including the important object based on the position of the distal end of the important object, and control display of the region of interest in the display area of the display device.

(12)

The medical image processing system according to (11), wherein the medical imaging device generates both a left and a right medical image corresponding to the medical image using three dimensional imaging.

(13)

The medical image processing system according to (11) to (12), wherein the controller including the circuitry is configured to determine the position of the distal end of the important object within the medical image by detecting the position of the distal end of the important object using a depth image generated from the left and right medical images.

(14)

The medical image processing system according to (11) to (13), wherein the important object is a surgical instrument and the medical imaging device is an endoscope or a surgical microscope.

(15)

A medical image processing apparatus, comprising:
a controller including circuitry configured to
determine a position of an important area within a medical image,
estimate a region of interest within the medical image adjacent to a region including the important area based on the position of the important area, and
control display of the region of interest.

(16)

The medical image processing apparatus according to (15), wherein the region of interest within the medical image is distinct from the region including the important area.

(17)

An image processing apparatus including: a generation section configured to generate depth information of an image from the image obtained by imaging a surgical field which includes a region of a surgical target; and a position detection section configured to detect a three-dimensional position of a surgical instrument by using the generated depth information of the image.

(18)

The apparatus according to (17), further including: a remarkable point estimation section configured to estimate a remarkable point for a practitioner operating the surgical instrument, based on the detected three-dimensional position of the surgical instrument and the depth information.

(19)

The apparatus according to (18), further including: a focus control section configured to output a focus control signal such that a focus coincides with the remarkable point estimated by the remarkable point estimation section.

(20)

The apparatus according to (18), in which the remarkable point estimation section estimates an intersection point to be the remarkable point, the intersection point of the surgery region and an extension line obtained by extending a line segment corresponding to the three-dimensional position of the surgical instrument.

(21)

The apparatus according to (18), in which a predetermined mark for indicating the remarkable point is superposed on the image obtained by the imaging section.

(22)

The apparatus according to (19), in which the focus control section controls the focus when an instruction from the practitioner is received, and the instruction from the practitioner is generated by an operation of a foot pedal or a button included in the surgical instrument or utterance of a predetermined word.

(23)

The apparatus according to any one of (17) to (22), in which the generation section generates the depth information from a predetermined area of the image positioned on extension of a tip end portion of the surgical instrument which is detected by the position detection section.

(24)

The apparatus according to (21), in which an extension line is also superposed and displayed on the image, the extension line being obtained by extending a line segment corresponding to the three-dimensional position of the surgical instrument.

(25)

The apparatus according to any one of (17) to (24), in which the position detection section detects the three-dimensional position of the surgical instrument based on information on a linear edge in the image.

(26)

The apparatus according to any one of (17) to (25), in which the position detection section detects the three-dimensional position of the surgical instrument based on information on a specific color in a parallax image.

(27)

The apparatus according to any one of (17) to (26), in which the position detection section detects the three-dimensional position of the surgical instrument by detecting a mark marked on the surgical instrument from the image.

(28)

An image processing method including: causing an image processing apparatus to generate depth information of an image from the image obtained by imaging a surgical field which includes a region of a surgical target and to detect a three-dimensional position of the surgical instrument by using the generated depth information of the image.

(29)

A program of causing a computer to execute a process including: generating depth information of an image from the image obtained by imaging a surgical field which includes a region of a surgical target; and detecting a three-dimensional position of the surgical instrument by using the generated depth information of the image.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

11 Endoscope Camera head
12 CCU
13 Operation section
14 Display
21 Imaging section
24a First imaging sensor
24b Second imaging sensor
41 Depth information generation section
42 Forceps/area position detection section
43 Remarkable point estimation section
44 Image superposition section
45 Operation control section
61 Foot pedal
Q Remarkable point
QA Area of interest
111 Guide line
QB Zoom image
201 CPU
202 ROM
203 RAM
206 Input section
207 Output section
208 Storage section
209 Communication section
210 Drive

The invention claimed is:

1. A medical image processing apparatus, comprising:
a controller including circuitry configured to:
generate depth information of each location in a medical image from a right (R) image and a left (L) image supplied from an imaging section of the medical image processing apparatus using triangulation, determine a position of a distal end of an important object within the medical image by detecting a linear edge having a predetermined length or greater from a parallax image generated by the circuitry, wherein the linear edge is detected by detecting a difference between the important object and a surgical field within the medical image, estimate a region of interest within the medical image adjacent to a region including the important object based on the position of the distal end of the important object, and control display of the region of interest, wherein the controller including the circuitry is further configured to estimate the region of interest by detecting an estimated position of a cross point between an extension line from the distal end of the important object and a surface of a body, the extension line being in parallel with a longitudinal direction of the important object, wherein the position of the cross point is estimated by comparing the depth of each point along the extension line with the depth information of a corresponding location in the medical image until the depth information of a corresponding location in the medical image is less than the depth of a point along the extension line.

2. The medical image processing apparatus according to claim 1, wherein the medical image includes a surgical image of the body.

3. The medical image processing apparatus according to claim 1, wherein the region of interest within the medical image is distinct from the region including the important object.

4. The medical image processing apparatus according to claim 1, wherein the controller including the circuitry is configured to determine the position of the distal end of the important object within the medical image based on three dimensional position information of the important object.

5. The medical image processing apparatus according to claim 1, wherein the controller including the circuitry is configured to control display of the region of interest by displaying one or more of: a zoomed image corresponding to the region of interest, the medical image having focus on the region of interest, and the medical image in which the region of interest is highlighted.

6. The medical image processing apparatus according to claim 1, wherein the controller including the circuitry is configured to estimate the region of interest based on a three-dimensional posture of the important object.

7. The medical image processing apparatus according to claim 1, wherein the controller including the circuitry is configured to determine the position of the distal end of the important object within the medical image by detecting the position of the distal end of the important object using one or more of color difference information, edge detection techniques, brightness, and depth.

8. A method for processing a medical image by a medical image processing apparatus including a controller including circuitry, the method comprising:

generating, using the circuitry, depth information of each location in the medical image from a right (R) image and a left (L) image supplied from an imaging section of the medical image processing apparatus using triangulation, determining, using the circuitry, a position of a distal end of an important object within the medical image by detecting a linear edge having a predetermined length or greater from a parallax image generated by the circuitry, wherein the linear edge is detected by detecting a difference between the important object and a surgical field within the medical image;

estimating, using the circuitry, a region of interest within the medical image adjacent to a region including the important object based on the position of the distal end of the important object, wherein estimating the region of interest is performed by detecting an estimated position of a cross point between an extension line from the distal end of the important object and a surface of a body, the extension line being in parallel with a longitudinal direction of the important object, wherein the position of the cross point is estimated by comparing the depth of each point along the extension line with the depth information of a corresponding location in the medical image until the depth information of a corresponding location in the medical image is less than the depth of a point along the extension line; and controlling, using the circuitry, display of the region of interest.

9. A non-transitory computer readable medium having stored thereon a program that when executed by a computer causes the computer to implement a method for processing a medical image by a medical image processing apparatus including a controller including circuitry, the method comprising:

generating, using the circuitry depth information of each location in the medical image from a right (R) image and a left (L) image supplied from an imaging, section of the medical image processing apparatus using triangulation, determining, using the circuitry, a position of a distal end of an important object within the medical image by detecting a linear edge having a predetermined length or greater from a parallax image generated by the circuitry, wherein the linear edge is detected by detecting a difference between the important object and a surgical field within the medical image;

estimating, using the circuitry, a region of interest within the medical image adjacent to a region including the important object based on the position of the distal end of the important object, wherein estimating the region of interest is performed by detecting an estimated position of a cross point between an extension line from the distal end of the important object and a surface of a body, the extension line being in parallel with a longitudinal direction of the important object, wherein the position of the cross point is estimated by comparing the depth of each point along the extension line with the depth information of a corresponding location in the medical image until the depth information of a corresponding location in the medical image is less than the depth of a point along the extension line; and controlling, using the circuitry, display of the region of interest.

10. A medical image processing system, comprising:
a medical imaging device that obtains a medical image;
a display device having a display area; and
a controller including circuitry configured to
generate depth information of each location in the medical image from a right (R) image and a left (L) image supplied from an imaging section of the medical imaging device using triangulation, determine a position of a distal end of an important object within the medical image obtained by the medical imaging device by detecting a linear edge having a predetermined length or greater from a parallax image generated by the circuitry, wherein the linear edge is detected by detecting a difference between the important object and a surgical field within the medical image, estimate a region of interest within the medical image adjacent to a region including the important object based on the position of the distal end of the important object, and control display of the region of interest in the display area of the display device, wherein the controller including the circuitry is further configured to estimate the region of interest by detecting an estimated position of a cross point between an extension line from the distal end of the important object and a surface of a body, the extension line being in parallel with a longitudinal direction of the important object, wherein the position of the cross point is estimated by comparing the depth of each point along the extension line with the depth information of a corresponding location in the medical image until the depth information of a corresponding location in the medical image is less than the depth of a point along the extension line.

11. The medical image processing system according to claim 10, wherein the medical imaging device generates both a left and a right medical images corresponding to the medical image using a three dimensional imaging.

12. The medical image processing system according to claim 11, wherein the controller including the circuitry is configured to determine the position of the distal end of the important object within the medical image by detecting the position of the distal end of the important object using a depth image generated from the left and right medical images.

13. The medical image processing system according to claim 10, wherein the important object is a surgical instrument and the medical imaging device is an endoscope or a surgical microscope.

14. A medical image processing apparatus, comprising:
a controller including circuitry configured to:
generate depth information of each location a medical image from a right (R) image and a left (L) image supplied from an ging section of the medical image processing apparatus using triangulation, determine a position of an important area within the medical image by detecting differences between the important area and a surgical field within the medical image, estimate a region of interest within the medical image adjacent to a region including the important area based on the position of the important area, and control display of the region of interest, wherein the controller including the circuitry is further configured to estimate the region of interest by detecting an estimated position of a cross point between an extension line from the distal end of the important area and a surface of a body, the extension line being in parallel with a longitudinal direction of the important area, wherein the position of the cross point is estimated by comparing the depth of each point along the extension line with the depth information of a corresponding location in the medical image until the depth information of a corresponding location in the medical image is less than the depth of a point along the extension line.

15. The medical image processing apparatus according to claim 14, wherein the region of interest within the medical image is distinct from the region including the important area.

* * * * *